(12) United States Patent
Zhang

(10) Patent No.: US 10,533,942 B2
(45) Date of Patent: Jan. 14, 2020

(54) SYSTEM AND METHOD FOR MEASURING OIL CONTENT IN WATER USING LASER-INDUCED FLUORESCENT IMAGING

(71) Applicant: Jianfeng Zhang, Sugar Land, TX (US)

(72) Inventor: Jianfeng Zhang, Sugar Land, TX (US)

(*) Notice: Subject to any disclaimer, the term of this patent is extended or adjusted under 35 U.S.C. 154(b) by 149 days.

(21) Appl. No.: 15/632,347

(22) Filed: Jun. 25, 2017

(65) Prior Publication Data
US 2017/0292913 A1    Oct. 12, 2017

Related U.S. Application Data

(63) Continuation-in-part of application No. 14/455,907, filed on Aug. 10, 2014, now abandoned.

(51) Int. Cl.
*G01N 21/64* (2006.01)
*G01N 33/28* (2006.01)
*G01N 33/18* (2006.01)

(52) U.S. Cl.
CPC ..... *G01N 21/6402* (2013.01); *G01N 33/2847* (2013.01)

(58) Field of Classification Search
CPC ........... G01N 21/6402; G01N 33/2847; G01N 15/0227; G01N 2015/003; G01N 21/643; G01N 21/6458; G01N 33/1833; G02B 21/0076; G02B 21/008
USPC ........ 348/80; 356/432–436, 441, 241.1, 626, 356/627; 73/152.01, 152.55
See application file for complete search history.

(56) References Cited

U.S. PATENT DOCUMENTS

| | | | |
|---|---|---|---|
| 5,381,002 A | 1/1995 | Morrow | |
| 2007/0035736 A1* | 2/2007 | Vannuffelen | E21B 49/08 356/432 |
| 2009/0273774 A1 | 11/2009 | Sieracki | |
| 2015/0081228 A1* | 3/2015 | Krishnan | G01N 15/1031 702/29 |
| 2015/0293336 A1* | 10/2015 | Cohen | G02B 21/0044 359/385 |

OTHER PUBLICATIONS

D. Biggs, 3D Deconvolution Microscopy, 2010, Curr. Protec. Cytom., pp. 1-20. (Year: 2010).*
Jianfeng Zhang, Subsea Produced Water Sensor Development, RPSEA / SPE-GCS Ultra-Deepwater Technology Conference, Sep. 9-10, 2015,.Houston, TX.

* cited by examiner

*Primary Examiner* — Christopher S Kelley
*Assistant Examiner* — Kathleen M Walsh
(74) *Attorney, Agent, or Firm* — Ingenium Patents LLC; Peter R. Kramer

(57) ABSTRACT

The invention is a system and method to measure oil content in water utilizing the fluorescence of oil emitted under excitation by laser. Oil and water mixture is transferred through the system to a measurement section in a microscope, which produces high resolution 3-dimensional images of the oil and water mixture with the fluorescence. The images are analyzed to calculate the amount of oil in water and oil droplets distribution. The image is also analyzed to distinguish oil coated solids from oil droplets, and to calculate the sizes and volumes of the solids.

21 Claims, 2 Drawing Sheets

Figure 1:
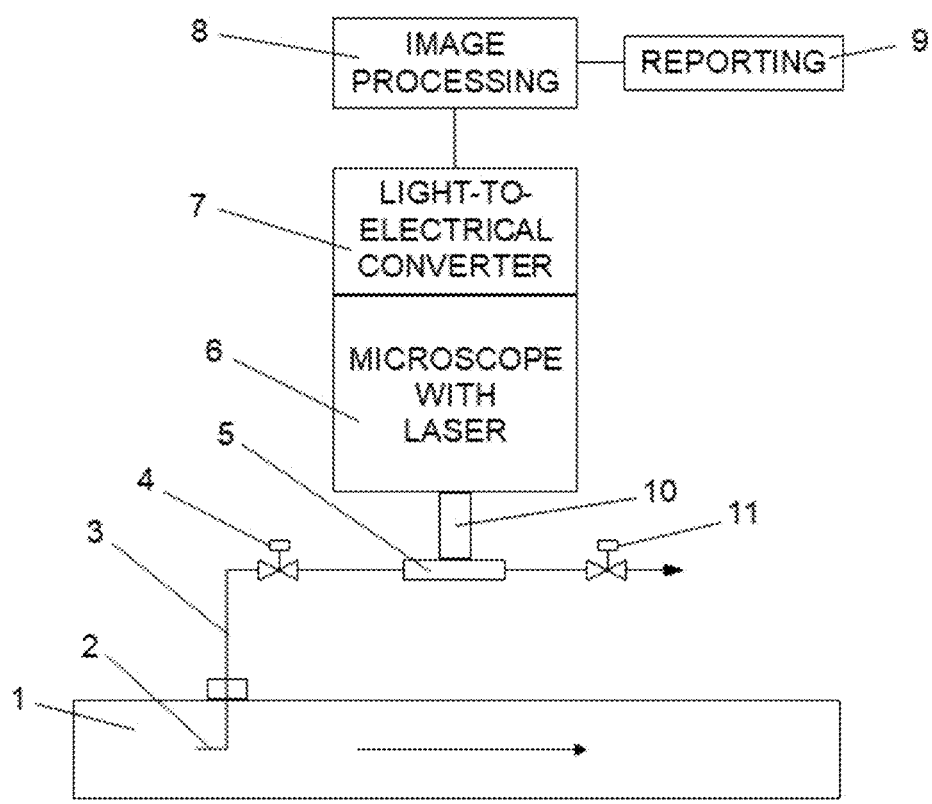

SYSTEM AND METHOD FOR MEASURING OIL CONTENT IN WATER USING LASER-INDUCED FLUORESCENT IMAGING

CROSS-REFERENCE TO RELATED APPLICATIONS

This application is a Continuation-In-Part of Nonprovisional application Ser. No. 14/455,907 filed Aug. 10, 2014 and claims priority benefit of application Ser. No. 14/455,907 filed and Provisional Application 61/867,056 filed on Jul. 17, 2013. Nonprovisional application Ser. No. 14/455,907 claimed benefit of the filing date of Provisional Application 61/867,056. The contents of application Ser. Nos. 14/455,907 and 61/867,056 are expressly incorporated herein by reference. In the event of any inconsistency between the definitions of terms between the current application and the prior applications, the definitions of the current application shall be used and the definitions in the prior applications shall no longer apply.

BACKGROUND OF THE INVENTION

Water is frequently produced with oil and gas production. The produced water is treated and disposed. The oil in water concentration is a key parameter to measure to determine the quality of the produced water. In addition to laboratory measurements of produced water quality, field measurements have also been applied for monitoring of the water quality with both bench-top and online methods.

Field of the Invention

The field of the invention is devices and methods for the measurement of oil content in water, especially as it relates to the measurement of oil content in water produced from petroleum and natural gas reservoirs.

Description of Related Art Including Information Disclosed Under 37 CFR 1.97 and 1.98

A listing of related art follows:
U.S. Pat. No. 7,935,938 B2, Apparatus for Measuring Fluorescent Material in A Liquid, 2011
U.S. Pat. No. 7,248,363 B2, Particle Size Analyzer, 2007
U.S. Pat. No. 6,525,325 B1, System for Quantifying the Hydrocarbon Content of Aqueous Media, 2003
European Patent EP 0 997 732 A1, Method and Equipment for Continuous Measurement of Mineral Oils in Water by Means of Spectrophotometric Detector, 1999
U.S. Pat. No. 5,381,002, Fluorescence Method of Quantifying Hydrocarbons, Including Crude Oil, Dispersed in Water, 1993
U.S. Pat. No. 4,953,978, Particle Size Analysis Utilizing Polarization Intensity Differential Scattering, 1990
U.S. Pat. No. 7,933,018 Spectral Imaging for Downhole Fluid Characterization, 2011

Prior to the current invention and in the relevant field of endeavor, fluorescence has only been used for emission magnitude measurement. Imaging analysis has only been used on images obtained by direct lighting and reflection which did not involve isolation of fluorescence emissions. None of these systems can provide 3-dimensional images.

BRIEF SUMMARY OF THE INVENTION

The present invention, described below, is a system and method which has higher image resolution to detect oil droplets as small as 0.25 micron in size, which is much smaller than the capabilities of the current systems and prior art, and can produce 3-dimensional images of the oil and water mixture. These features can improve the accuracy of measurements to include small droplets and to properly account for the droplets that may be behind other droplets in the view direction.

The present invention is an oil in water content measurement system and method which utilize laser fluorescence microscopy to generate one or more images, and analyze the images to determine the oil droplet content by the number and size distribution of the droplets. The images can also detect oil coated sand and other solid particles. The images can be 3-dimensional for configurations intended for high measurement accuracy, and 2-dimensional for configurations where lower accuracy at higher speed of measurement is desired. For the purposes of this application the term laser fluorescence microscopy, including confocal methods, denotes microscopy methods employing laser excitation with detection and imaging of fluorescence emissions from the sample under observation wherein the fluorescence emissions are optically isolated or separated from reflected, retransmitted, and backscattered light, i.e., a fluorescence only image. The lexicography given above is consistent with the meaning of laser fluorescence microscopy as a term of art that would be understood by a person or ordinary skill in the art at the time of the invention.

In one embodiment a sample is taken up into a measurement section having two valves. Once the measurement section is filled, the valves close and the sample is scanned after a predetermined period of time, preferably about 10 seconds to 5 minutes, sufficient for water motion to effectively cease to allow imaging with the system with resolution of up to 250 nanometers. The time period can be adjusted for even greater resolution than 250 nm. Successive view volumes are scanned with each view volume being divided into a number of focal planes which are individually scanned. Fluorescence emissions are captured by a CCD or other 2-dimensional imaging sensor which obtain the light magnitude at multiple pixels each time, or a photon multiplier tube which generates the light magnitude at a single pixel each time, and an image processing unit analyzes stacks of 2-D images for oil content and particle size distribution with results communicated by means of a reporting device.

BRIEF DESCRIPTION OF THE SEVERAL VIEWS OF THE DRAWING(S)

Figure 2:
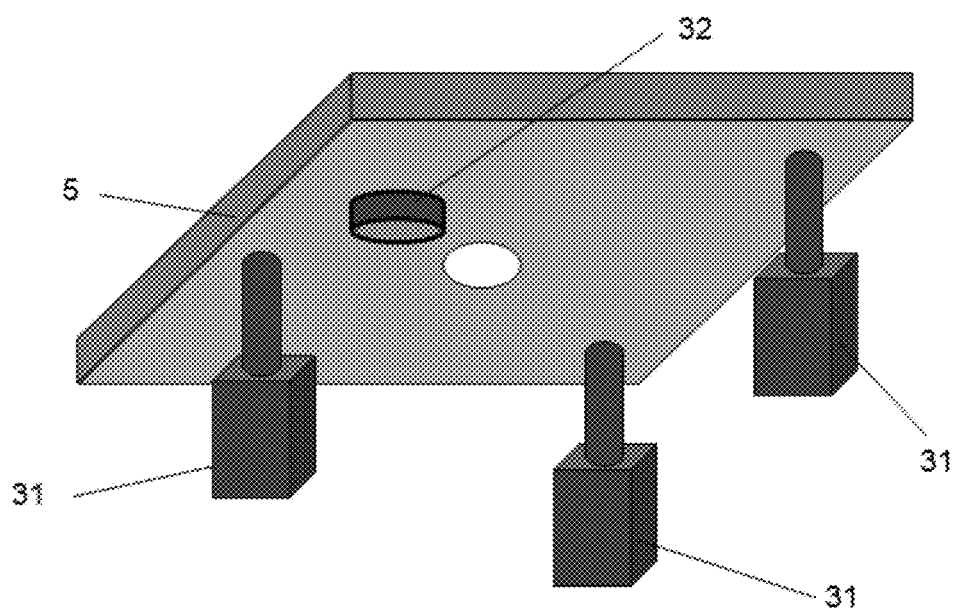

FIG. 1 Is a schematic diagram of an embodiment of the current invention.
FIG. 2 is a perspective view showing leveling devices affixed to a measurement section

DETAILED DESCRIPTION OF THE INVENTION

The inventor has discovered that the fluorescent properties of certain components of oil, such as the polycyclic aromatic hydrocarbons which emits fluorescent light when experiencing excitation by laser light, can be used to produce an image with a microscope. The inventor also discovered that the image can have very high resolution (250 nanometer or even finer) and 3-dimensional, and can be analyzed with an image analysis algorithm to determine the oil droplets' number, size distribution and volume. The inventor further discovered that the method can be used to measure the number, sizes, shape and volume of oil coated solid particles.

The measurement setup of the new method is illustrated in FIG. 1, where Item 1 is a conduit carrying produced water to discharge, re-injection or to other locations. A produced water sampling device 2, such as a tube, is inserted at the appropriate location within the produced water conduit 1. Piping 3 fluidly couples the sampling device with a valve 4. Valve 4 can be opened or closed to allow the sampled fluid from 3 to enter measurement section 5 or isolate the sample in measurement section 5 where the sample resides and is scanned by the microscope 6. Valve 11 works together with valve 4 (opened or closed) to allow the sampled fluid from 3 to enter measurement section 5 or isolate the sample in measurement section 5. The two valves are capable of repeated open and close cycle operation as fast as 10 seconds per cycle. A microscope objective 10 optically couples the measurement section to microscope 6. The objective can be positioned outside the view section, in which case the measurement section has a viewing window, or can be positioned inside the measurement section. The microscope includes a laser source. A particularly preferred microscope is laser fluorescence confocal microscope. A light-to-electrical converter 7 converts the fluorescent emission signal to electrical signal. A particularly preferred light-to-electrical converter is a charge-coupled device (CCD). An image processing unit 8 receives electrical signals from the light-to-electrical converter. A particularly preferred image processing configuration is with a computer at the measurement site. Another particularly preferred configuration is a computing system embedded in the microscope body or a camera body. Another preferred configuration is a computer at a remote site, which is connected with the camera with signal linkage. The image processing unit uses one or more algorithms to process the image, such as with the particularly preferred method of deconvolution, and identify the objects in the image as oil droplets, solid particles, or other. Results are conveyed to a user by a reporting device 9 for the user to obtain the determined oil droplets and other particles' sizes, shapes and volumes.

The water sampling device 2 is inserted to the produced water discharge pipe 1 for a slip stream to be flown through the sample piping 3, valves 4 and 11, measurement section 5 and to discharge. The measurement section is instrumented with a microscope 6 with laser, such as the particularly preferred spinning disk laser confocal microscope with a scanning unit with lenslet. The microscope illuminates the view volume with laser beam in a scanning manner. The fluorescence generated by the oil droplets in the sample is captured by the light to electrical signal converter 7, a particularly preferred configuration for which is a CCD (charge-coupled device). The digital signals from the converter are sent to an image processing computing device 8 which can be located either at the site, at a remote location. The image processing utilizes algorithms to improve the image quality if needed, for example using the particularly preferred algorithms of deconvolution, to remove the noise caused by light contributions from out-of-focal plane locations. The processed signals are analyzed to determine the location and size of the oil droplets in the sample. The total volume fraction of the oil droplets and the size distribution are reported through the human machine interface 9.

The measurement section is optimally supported with a leveling mechanism as shown in FIG. 2. The leveling mechanism includes a level indicator 32 and three height-adjustable piezoelectric or stepping motor leveling supports 31 which are attached to the measurement section 5. Each leveling support has a rod 35 connected to a piezoelectric base portion 37. The base portions can be fixed to suitable locations which do not move as the height of the leveling supports are adjusted. Alternatively, the piezoelectric base portion can be directly attached to the measurement section.

Many measurement sequences can be utilized with the present invention. An example measurement sequence is as follows:

1. The valves in the sampling flow path are opened to initiate the measurement operation;
2. After a period of pre-determined time, the flow in the measurement section reaches equilibrium, and the valves are closed;
3. Wait for a pre-determined period of time, which is selected for the particular combination of measurement section design, water characteristics, environment parameters, and other factor, typically 10 seconds to 5 minutes until motion of the sample in the measurement section is sufficiently diminished for scanning. At this time the scanning of the sample can begin;
4. One view volume is chosen for scanning. The laser beams excite the aromatic hydrocarbon molecules in the oil droplets to generate fluorescent emissions. The fluorescent emissions are captured by the converter (CCD as one example). Once one focal plane has been scanned (one frame), the adjacent focal plane is selected. This repeats until the sample volume has been completely scanned;
5. Another view volume is chosen and scanned. This repeats until all the view volumes are scanned;
6. The captured signals are processed by the image processing unit for oil content and particle size distribution readout;
7. The valves are opened to discharge the sample;
8. The measurement unit is ready for the next measurement.

Many variations of the measurement configuration and image processing method are possible, including:

The measurement section is not fluidly coupled with the sampling path, instead, it is a separate sample contained in a transparent device under the objective, similar to a typical microscope configuration. Thus, the method can be utilized in a laboratory on separately collected and prepared samples;

The microscope is a wide-field laser fluorescence microscopy, a multi-photon microscope;

The image analysis unit uses the stack of 2-D images from the light to electrical signal converter directly, without first performing noise reduction, for object identification;

The image analysis unit uses deconvolution on the images collected by the wide field microscope;

Only the 2-D image of a single focal plane is taken at each location for increasing the scanning speed.

The description above has disclosed the specifics of the present invention to measure oil content in water. It should be apparent to those skilled in the art that many other variations and modifications are possible which are within the spirit of the disclosed invention.

I claim:

1. An apparatus for measuring oil content in an aqueous fluid configured to produce high resolution images with fluorescence comprising,
   a microscope objective,
   a measurement section,
   a first valve and a second valve configured to isolate a sample of the aqueous fluid such that water motion is effectively abolished to allow imaging with the apparatus with resolution of up to 250 nanometers and to permit entry of the aqueous fluid into said measurement section and to permit discharge therefrom, said measurement section further configured to allow an optical path between said measurement section and said microscope objective, a laser fluorescence microscope, with said microscope objective operatively coupled to said microscope, a light to electrical signal converter configured to convert fluorescence emissions to electrical signals, said apparatus configured to commence laser illumination of said aqueous fluid after a predetermined period of time following entry of the aqueous fluid, said period of time being about 10 seconds to 5 minutes, an image processing unit operatively connected to said electrical signal converter, said image processing unit comprised of a computer programmed for image processing to identify objects from an image or from a plurality of images obtained from said electrical converter as oil droplets, solid particles or other objects.

2. The apparatus of claim 1 further comprising, a scanning unit.

3. The apparatus of claim 2 wherein said laser fluorescence microscope is a laser fluorescence confocal microscope.

4. The apparatus of claim 3 wherein said laser fluorescence confocal microscope is a spinning disk laser fluorescence confocal microscope, said spinning disk laser fluorescence confocal microscope further comprising a lenslet, wherein said scanning unit is further comprised of said lenslet.

5. The apparatus of claim 4 further comprising, a charge-coupled device, said electrical signal converter being comprised of said charge-coupled device.

6. The apparatus of claim 3 further comprising, wherein said image processing unit is further configured to use the method of deconvolution to generate a 3-dimensional image and to identify objects in the 3-dimensional image, said 3-dimensional image being obtained by using a stack of 2-D images, said stack of 2-D images comprised of said plurality of images obtained from said electrical signal converter without first performing noise reduction.

7. The apparatus of claim 6 further comprising, a charge-coupled device, said electrical signal converter being comprised of said charge-coupled device.

8. The apparatus of claim 2 wherein said laser fluorescence microscope is a multi-photon laser fluorescence microscope.

9. The apparatus of claim 8 wherein said light to electrical signal converter is a charge-coupled device.

10. The apparatus of claim 1 further comprising wherein said laser fluorescence microscope is a wide-field laser fluorescence microscope.

11. The apparatus of claim 10 further comprising, a charge-coupled device, said electrical signal converter being comprised of said charge-coupled device.

12. A method for measuring oil content in an aqueous fluid using an apparatus configured to generate images with fluorescence comprising, introducing the aqueous fluid into a flow path with means configured to introduce the aqueous fluid into the flow path, isolating a sample in a measurement section, holding the sample for 10 seconds to 5 minutes, capturing an image or a plurality of images, the image capturing step comprising,
a) illuminating the sample with a laser fluorescence microscope, said laser fluorescence microscope configured to optically separate fluorescence emissions from reflected, retransmitted and backscattered light,
b) directing fluorescence emissions to a light-to-electrical signal converter, the signal converter being configured to convert fluorescence emissions to electrical signals thereby generating either a 2-dimensional image or a plurality of 2-dimensional images, analyzing said 2-dimensional image or said plurality of 2-dimensional images with an image processing unit, said image processing unit being operatively connected to said electrical signal converter, said image processing unit being programmed to identify objects in the sample as oil droplets, solid particles or other objects.

13. The method of claim 12 wherein the image capturing is performed with said laser fluorescence microscope having a scanning unit.

14. The method of claim 13 wherein the image capturing step is performed with said laser fluorescence microscope being a confocal laser fluorescence microscope.

15. The method of claim 14 wherein the image capturing step is performed wherein said scanning unit is further comprised of a lenslet.

16. The method of claim 15 wherein the image capturing step is performed with said light-to-electrical signal converter comprised of a charge-coupled device.

17. The method of claim 16 further comprising, generating high resolution 3-dimensional images from said plurality of 2-dimensional images thereby identifying the objects in the sample.

18. The method of claim 17 wherein the image capturing step is performed with said light-to-electrical signal converter further comprised of a charge-coupled device.

19. The method of claim 18 wherein the illuminating step is performed with said laser fluorescence microscope further comprised of a multi-photon laser fluorescence microscope.

20. The method of claim 12 wherein the illuminating step is performed with said laser fluorescence microscope further comprised of a wide-field laser fluorescence microscope.

21. The method of claim 20 wherein the image capturing step is performed with said light-to-electrical signal converter further comprised of a charge-coupled device.

\* \* \* \* \*